United States Patent
Oh et al.

(10) Patent No.: US 9,198,613 B2
(45) Date of Patent: Dec. 1, 2015

(54) APPARATUS AND METHOD OF DIAGNOSING HEALTH BY USING VOICE

(71) Applicant: SAMSUNG ELECTRONICS CO., LTD., Suwon-si (KR)

(72) Inventors: Hee-jin Oh, Suwon-si (KR); Yong-tae Kim, Seongnam-si (KR); Hwan Shim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/735,766

(22) Filed: Jun. 10, 2015

(65) Prior Publication Data

US 2015/0282756 A1    Oct. 8, 2015

Related U.S. Application Data

(63) Continuation of application No. 13/397,744, filed on Feb. 16, 2012, now Pat. No. 9,055,861.

(60) Provisional application No. 61/447,183, filed on Feb. 28, 2011.

(30) Foreign Application Priority Data

Sep. 8, 2011    (KR) .......................... 10-2011-0091316

(51) Int. Cl.
*A61B 5/00*    (2006.01)
*A61B 7/00*    (2006.01)
*A61B 7/04*    (2006.01)

(52) U.S. Cl.
CPC ............. *A61B 5/4803* (2013.01); *A61B 5/7246* (2013.01); *A61B 7/00* (2013.01); *A61B 7/003* (2013.01); *A61B 7/04* (2013.01)

(58) Field of Classification Search
CPC ............ A61B 7/00; A61B 7/003; A61B 7/04; A61B 5/4803; A61B 5/7246
See application file for complete search history.

(56) References Cited

U.S. PATENT DOCUMENTS

| | | | |
|---|---|---|---|
| 3,752,929 | A | 8/1973 | Fletcher |
| 6,427,137 | B2 | 7/2002 | Petrushin |
| 7,529,670 | B1 | 5/2009 | Michaelis |
| 7,688,621 | B2 | 3/2010 | Cho et al. |
| 8,100,839 | B2 | 1/2012 | Galkin |
| 8,287,470 | B2 | 10/2012 | Kandori et al. |
| 8,494,857 | B2 | 7/2013 | Pakhomov |

(Continued)

FOREIGN PATENT DOCUMENTS

| | | |
|---|---|---|
| KR | 1020030018689 A | 3/2003 |
| KR | 1020030031076 A | 4/2003 |

(Continued)

*Primary Examiner* — Max Hindenburg
(74) *Attorney, Agent, or Firm* — Sughrue Mion, PLLC

(57) ABSTRACT

A method and apparatus for diagnosing a user's health state are provided. The apparatus includes including a voice detecting unit which detects and monitors a user's voice; a voice analyzing unit which extracts a voice feature from a voice detected by the voice detecting unit, based on a health state to be diagnosed; a voice diagnosing unit which diagnoses a health state of the user by comparing the voice feature extracted by the voice analyzing unit with an abnormal state reference, and which monitors a change in the health state; and a diagnosis outputting unit which outputs information regarding the health state and a health state change diagnosed by the voice diagnosing unit.

18 Claims, 9 Drawing Sheets

(56) References Cited

U.S. PATENT DOCUMENTS

| | | |
|---|---|---|
| 8,583,207 B2 | 11/2013 | Tsai et al. |
| 2008/0300867 A1 | 12/2008 | Yan |

FOREIGN PATENT DOCUMENTS

| | | |
|---|---|---|
| KR | 1020040076099 A | 8/2004 |
| KR | 1020040105008 A | 12/2004 |
| KR | 1020060066416 A | 6/2006 |

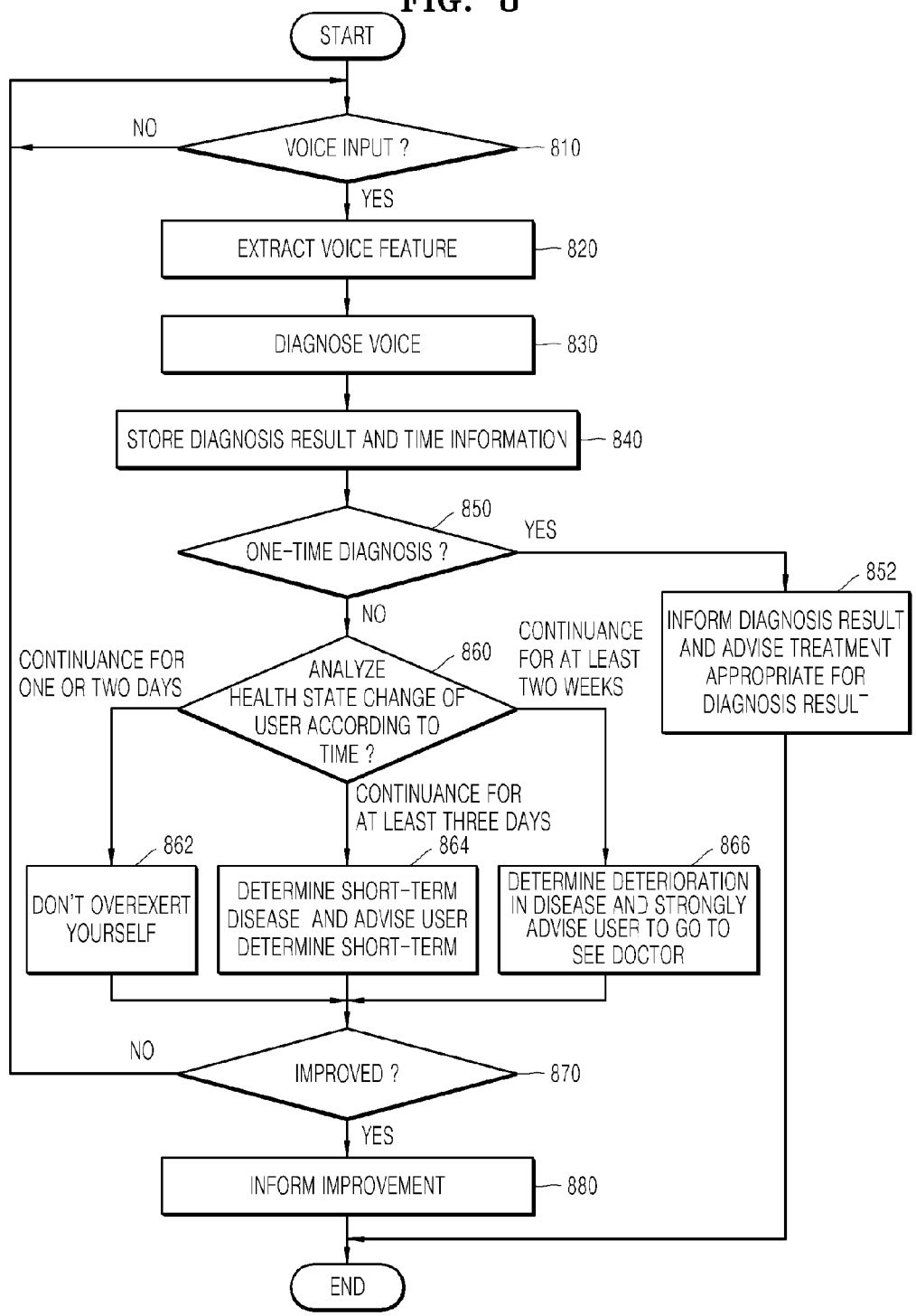

FIG. 9B

| NORMAL VOICE | | shimmer | MFCC 2 | MFCC 3 |
|---|---|---|---|---|
| Gaussian 1 | mean | 1.159092 | 1.612643 | −0.96954 |
| | variance | 0.275863 | 0.559883 | 0.722929 |
| | weight | 0.697673247 | | |
| Gaussian 2 | mean | 1.91949 | 1.669363 | −1.60919 |
| | variance | 1.14742 | 0.35281 | 0.394539 |
| | weight | 0.302326753 | | |

| ABNORMAL VOICE | | shimmer | MFCC 2 | MFCC 3 |
|---|---|---|---|---|
| Gaussian 1 | mean | 1.498629 | 2.262902 | −0.29777 |
| | variance | 20.70575 | 0.678287 | 0.79613 |
| | weight | 0.294951374 | | |
| Gaussian 2 | mean | 3.116301 | 2.017525 | 0.24371 |
| | variance | 1.757901 | 0.50225 | 0.316895 |
| | weight | 0.705048626 | | |

APPARATUS AND METHOD OF DIAGNOSING HEALTH BY USING VOICE

CROSS-REFERENCE TO RELATED PATENT APPLICATION

This application is a continuation of U.S. patent application Ser. No. 13/397,744, filed on Feb. 16, 2012 in the U.S. Patent and Trademark Office, which claims the benefit of U.S. Provisional Patent Application No. 61/447,183, filed on Feb. 28, 2011, in the U.S. Patent and Trademark Office, and priority from Korean Patent Application No. 10-2011-0091316, filed on Sep. 8, 2011, in the Korean Intellectual Property Office, the disclosures of which are incorporated herein in their entireties by reference.

BACKGROUND

1. Field

Apparatuses and methods consistent with exemplary embodiments relate to a method and apparatus for diagnosing health, and more particularly, to a method and apparatus for diagnosing states of human organs by using a voice.

2. Description of the Related Art

Recently, many people have symptoms of occipital pain and a resultant change in voice due to environmental and lifestyle factors such as air pollution, activities in a limited space, and an increase in use of mobile phones. If a problem associated with the occipital bone is not treated at an early stage and thus the bone becomes deformed or there is a malignant growth, the problem may only be solved through surgery to enable a person to have a chance at recovering his/her normal voice. Thus, an early diagnosis of problems effecting the occipital bone is important to preserve an occipital function, and to increase rates of successful treatment and survival rates of patients.

A wide range of diseases, including Parkinson's disease can be diagnosed by using a patient's voice. Parkinson's disease is caused when cells which produce dopamine, which is a neurotransmitter secreted in a region of the brain that controls movement, die, and symptoms of Parkinson's disease include issues including muscle rigidity, body shaking, slowed movements, and impaired balance.

However, at a time when a person can be diagnosed based on such symptoms, many dopamine-producing cells have already died. Thus, in order to improve treatment efficacy by preventing the death of dopamine-producing cells, early diagnosis is important. A study has proved that Parkinson's disease, which is a disease of the central nervous system, may be diagnosed early by analyzing a patient's vocal pattern to analyze features of the vocal pattern which are difficult for a person to distinguish. The range of health diagnoses which can be made based on such vocal analysis may be broadened.

Therefore, there is a need to provide a method and apparatus for diagnosing states of human organs by using vocal analysis.

SUMMARY

One or more exemplary embodiments may provide a method and apparatus for checking and diagnosing states of a patient's organs by analyzing the patient's voice.

According to an aspect of an exemplary embodiment, there is provided a health diagnosing apparatus including a voice detecting unit which detects and monitors a user's voice; a voice analyzing unit which extracts a voice feature from a voice detected by the voice detecting unit, based on a health state to be diagnosed; a voice diagnosing unit which diagnoses a health state of the user by comparing the voice feature extracted by the voice analyzing unit with an abnormal state reference, and which monitors a change in the health state; and a diagnosis outputting unit which outputs information regarding the health state and a health state change diagnosed by the voice diagnosing unit.

The voice detecting unit may monitor changes in a voice state of a user.

The voice detecting unit may include an analog-to-digital converter; and a voice detecting unit which detects a voice signal from a digital signal output by the analog-to-digital converter.

The voice analyzing unit may include a health state selecting unit which selects a health state type based on the voice detected by the voice detecting unit; a voice period selecting unit which selects a voice period for a diagnosis based on to the health state type selected by the health state selecting unit; a voice feature selecting unit which selects a voice feature based on the health state type selected by the health state selecting unit; and a voice feature extracting unit which extracts the voice feature from the voice of a user based on the voice feature selected by the voice feature selecting unit.

The voice feature extracting unit may include a normal voice database and an abnormal voice database so as to distinguish between a normal voice and an abnormal voice.

The voice diagnosing unit may include a comparing unit which compares the voice feature extracted by the voice analyzing unit with the abnormal state reference; a monitoring unit which detects a change over time in a voice state of the user; and a diagnosis processing unit which diagnoses a state of the user's health organs according to a result of the comparison by the comparing unit, and a change detected by the monitoring unit.

The health diagnosing apparatus may further include a storage unit which stores an output of the diagnosing processing unit and diagnosis time information.

The diagnosis outputting unit may include a digital signal processor which converts information regarding the health state and a health state change diagnosed by the voice diagnosing unit into one or more audio or video signals; a display unit which outputs a video signal converted by the digital signal processor; and a speaker which outputs an audio signal converted by the digital signal processor.

According to an aspect of another exemplary embodiment, there is provided a method of diagnosing a user's health, the method including: detecting and monitoring a voice of the user; extracting a voice feature from the detected voice, based on a health state type to be diagnosed; diagnosing a health state of the user by comparing the extracted voice feature with an abnormal state reference, and monitoring a change in the health state; and outputting information regarding the health state and the health state change.

The operation of detecting the voice may include converting an input voice into a digital voice signal; and detecting the voice of the user from the digital voice signal.

The operation of extracting the voice feature may include determining the health state type to be diagnosed; selecting a voice period for a diagnosis according to the health state type; selecting a voice feature corresponding to the health state type; and extracting the selected voice feature from the voice period.

The operation of diagnosing the health state may include analyzing a change over time in the health state; and outputting an advising message according to the change over time in the health state.

The operation of diagnosing the health state and monitoring the health state change may include comparing the extracted voice feature with the abnormal state reference; detecting a change over time in a voice state; and diagnosing states of the user's health according to a result of the comparison, and the change in the voice state.

The method may further include storing and updating a result of the diagnosing and diagnosis time information in a storage unit.

The method may further include an operation of deriving references with respect to an abnormal voice and a normal voice so as to compare the voice feature with the abnormal state reference.

The operation of deriving the references may include operations of forming an abnormal voice database and a normal voice database; extracting an abnormal voice feature and a normal voice feature from the abnormal voice database and the normal voice database, respectively: performing comparison training with respect to the extracted abnormal voice feature and the extracted normal voice feature; and deriving the abnormal state reference according to the comparison training.

The operation of outputting may include converting information regarding the health state and the health state change into one or more audio or video signals; and outputting the one or more audio or video signals.

BRIEF DESCRIPTION OF THE DRAWINGS

The above and/or other aspects and advantages will become more apparent by the following detailed description of exemplary embodiments with reference to the attached drawings in which:

FIG. 8 is a detailed flowchart of a method of diagnosing health, according to another exemplary embodiment;

FIG. 9B illustrates a diagnosing reference of Gaussian Mixture Model (GMM) parameters that are modelled by two Gaussian functions;

FIG. 10 is a flowchart of a method of diagnosing health, according to another exemplary embodiment of.

DETAILED DESCRIPTION

Hereinafter, exemplary embodiments will be described with reference to the attached drawings.

As used herein, the term "and/or" includes any and all combinations of one or more of the associated listed items.

Figure 1:
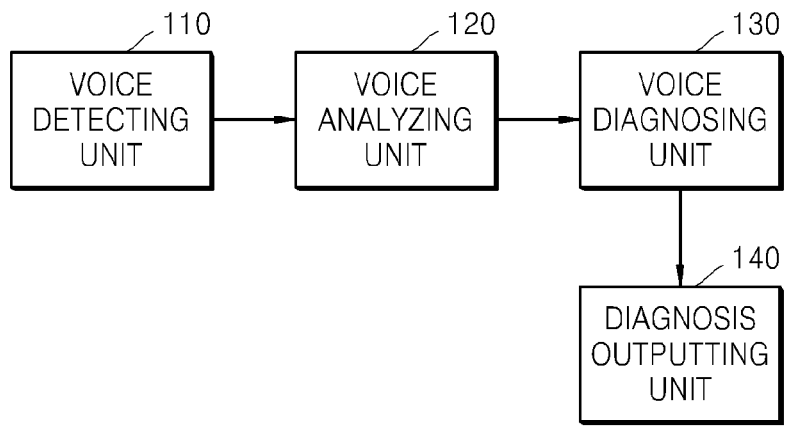
FIG. 1 is a block diagram of a health diagnosing apparatus according to an exemplary embodiment.

FIG. 1 is a block diagram of a health diagnosing apparatus according to an exemplary embodiment.

The health diagnosing apparatus may be one of any number of electronic apparatuses capable of recording a voice input, or having a telephone function. Examples of such electronic apparatuses include a TV, a mobile phone, a smart phone, a monitor connected to a CPU, a Voice over Internet Protocol (VoIP) telephone, a portable multimedia player (PMP), a personal digital assistant (PDA), a notebook computer, or the like, but are not limited thereto.

The health diagnosing apparatus of FIG. 1 includes a voice detecting unit 110, a voice analyzing unit 120, a voice diagnosing unit 130, and a diagnosis outputting unit 140.

The voice detecting unit 110 monitors and detects a user's voice via a user's recording or a phone conversation. Also, the voice detecting unit 110 additionally detects when a particular user is speaking (via the phone conversation and a voice-using game).

That is, the voice detecting unit 110 not detects when a particular use is speaking, but also constantly monitors a state of the user's voice for any changes even when the user is not aware of the monitoring.

The voice analyzing unit 120 extracts a voice feature for each type of health state from the voice detected by the voice detecting unit 110. Here, the voice analyzing unit 120 selects voice features capable of increasing an efficiency and performance of a diagnosis, and extracts the voice feature in consideration of a characteristic of electronic medical equipment that may have a limited calculation capacity and a limited memory.

The voice diagnosing unit 130 diagnoses the user's health by comparing the voice feature extracted by the voice analyzing unit 120 with an abnormal state reference and thereby monitors changes in the state of health of the user. Also, the voice diagnosing unit 130 can collect, update, and store diagnosis results.

The diagnosis outputting unit 140 converts information regarding the health of the user and any changes in the users state of health as diagnosed by the voice diagnosing unit 130 into a predetermined type of signal, and then outputs the signal to a speaker or a monitor. Here, the predetermined type of signal may include a graphic signal or an audio and/or a video signal.

Figure 2:
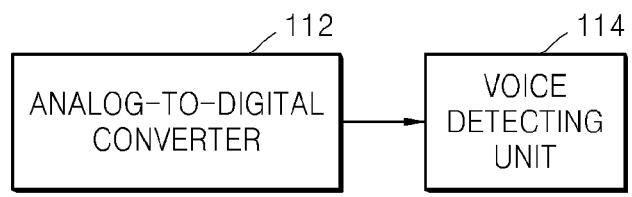
FIG. 2 illustrates an example of a voice detecting unit of FIG. 1.

FIG. 2 illustrates an example of the voice detecting unit 110 of FIG. 1.

The voice detecting unit 110 of FIG. 2 includes an analog-to-digital converter 112 and a voice detecting unit 114.

The analog-to-digital converter 112 converts an input analog signal into a digital signal.

The voice detecting unit 114 detects a voice signal from the digital signal output by the analog-to-digital converter 112.

An example of a method of detecting the voice signal may include voice activity detection (VAD) or end point detection (EPD).

Figure 3:
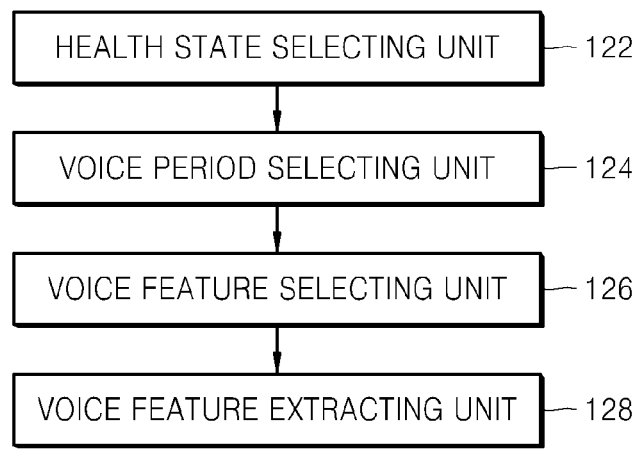
FIG. 3 illustrates an example of a voice analyzing unit of FIG. 1.

FIG. 3 illustrates an example of the voice analyzing unit 120 of FIG. 1.

The voice analyzing unit 120 of FIG. 3 includes a health state selecting unit 122, a voice period selecting unit 124, a voice feature selecting unit 126, and a voice feature extracting unit 128. The voice analyzing unit 120 may include one or more different configuring elements according to a desired diagnosis function.

In order to diagnose various states of health of the user based on the user's voice, the health state selecting unit 122 selects a type of health state to be diagnosed. For example, the health state type may include laryngeal cancer or Parkinson's disease.

The voice period selecting unit 124 selects a voice period of a user according to the health state type selected by the health state selecting unit 122. The voice period selecting unit 124 may selectively select the voice period of the user according to the selected health state type. For example, when laryngeal cancer is selected, only vowel portions are selected, and when the Parkinson's disease is selected, an entire sentence may be selected.

The voice feature selecting unit 126 selects a voice feature corresponding to the health state type selected by the health state selecting unit 122.

Exemplary, non-limiting voice features for use in distinguishing between a normal voice and an abnormal voice are Jitter (JITT), Shimmer (SHIMM), a Harmonics-to-Noise Ratio (HNR), and a Mel-Frequency Cepstral Coefficient (MFCC).

Here, JITT is an average variation of pitch, SHIMM is an average variation of amplitude, HNR is a ratio of a harmonic component to a noise component, and MFCC is a mathematical coefficient for sound modeling.

Typically, an average variation of an abnormal voice pitch is greater than an average variation of a normal voice pitch.

Typically, an average variation of abnormal voice amplitude is greater than an average variation of normal voice amplitude.

Typically, a ratio of a harmonic component to a noise component in an abnormal voice is greater than a ratio of a harmonic component to a noise component in a normal voice.

In a case in which laryngeal cancer is selected, the voice feature used to detect an abnormal voice may include JITT and SHIMM.

The voice feature extracting unit 128 extracts, from the voice of the user, the voice feature such as JITT, SHIMM, HNR or MFCC, which is selected by the voice feature selecting unit 126. The voice feature extracting unit 128 may extract the voice feature by using software or Mel-Frequency Cepstrum (MFC).

In order to distinguish between a normal voice and an abnormal voice, the voice feature extracting unit 128 includes a normal voice database and an abnormal voice database.

Figure 4:
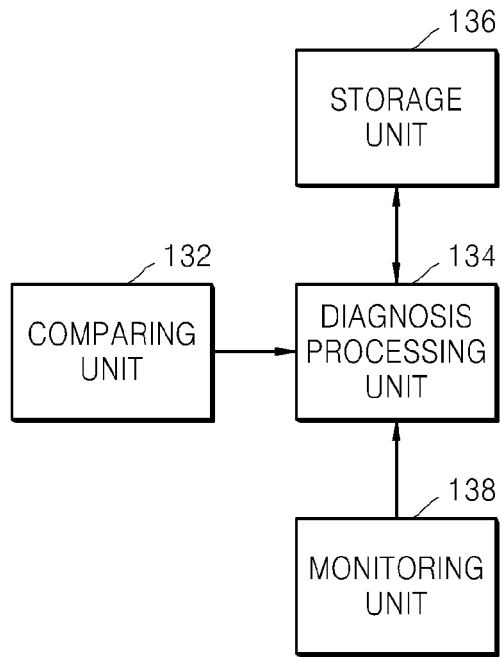
FIG. 4 illustrates an example of a voice diagnosing unit of FIG. 1.

FIG. 4 illustrates an example of the voice diagnosing unit 130 of FIG. 1.

The voice diagnosing unit 130 of FIG. 4 includes a comparing unit 132, a diagnosis processing unit 134, a storage unit 136, and a monitoring unit 138.

The comparing unit 132 compares the voice feature extracted by the voice analyzing unit 120 with an abnormal state reference. Here, the abnormal state reference is a diagnosis reference tool with which a diagnosis expert determines the states of a user's organs by referring to an objective voice feature. The diagnosis reference for distinguishing between the normal voice and the abnormal voice may be trained by using a Gaussian Mixture Model (GMM)/a Hidden Markov Model (HMM), a neural network, or the like.

The monitoring unit 138 detects a change in the state of the user's voice over time.

The diagnosis processing unit 134 diagnoses the states of a user's organs according to a result of the comparison by the comparing unit 132, and any changes in the state of the user's voice as monitored by the monitoring unit 138.

The storage unit 136 stores a result of the diagnosis performed by the diagnosis processing unit 134 and updates a diagnosis result. The storage unit 136 may be a magnetic recording medium such as a hard disk drive or may be a non-volatile memory such as an electrically erasable programmable read-only memory (EEPROM), a flash memory, or the like, the storage unit 136 is not limited to these examples.

Figure 5:
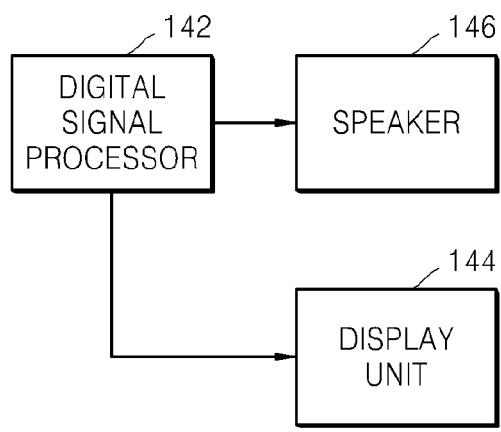
FIG. 5 illustrates an example of a diagnosis outputting unit of FIG. 1.

FIG. 5 illustrates an example of the diagnosis outputting unit 140 of FIG. 1.

The diagnosis outputting unit 140 of FIG. 5 includes a digital signal processor 142, a display unit 144, and a speaker 146.

The digital signal processor 142 converts information regarding the health state and any change in the health state, detected by the voice diagnosing unit 130, into audio and video signals.

The display unit 144 displays the video signal, which is processed by the digital signal processor 142, as a graphic image or a video image.

The speaker 146 outputs the audio signal processed by the digital signal processor 142.

Figure 6:
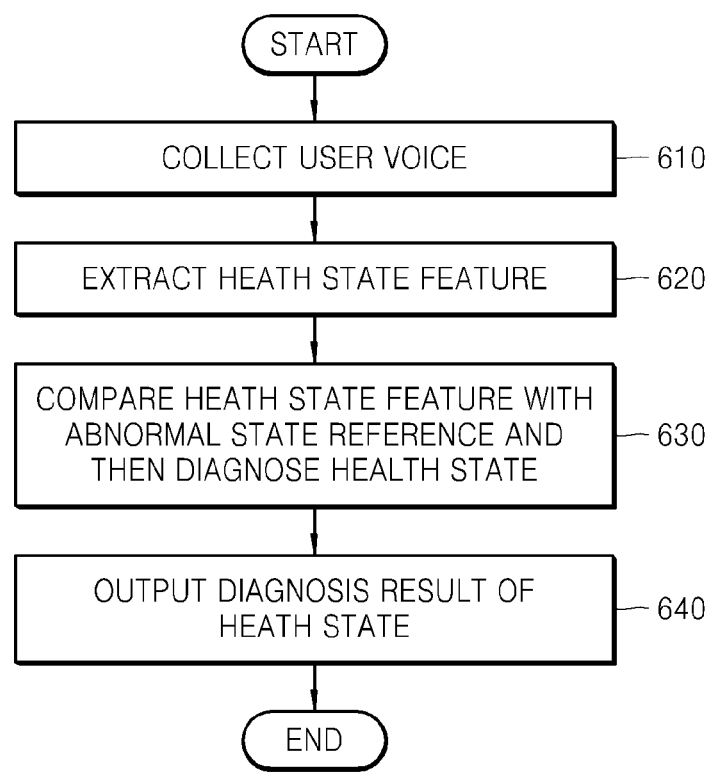
FIG. 6 is a flowchart of a method of diagnosing health, according to an exemplary embodiment.

FIG. 6 is a flowchart of a method of diagnosing health, according to an exemplary embodiment.

First, a user's voice input via a recording or a phone-conversation is detected and collected (operation 610).

With respect to each type of health state, a voice feature for distinguishing between a normal voice and an abnormal voice is selected from the collected user's voice (operation 620).

A health state is diagnosed by comparing the extracted voice feature with an abnormal state reference, and any change in the health state is monitored (operation 630).

Information regarding the diagnosed health state and the health state change is output as a notice signal (operation 640).

According to the present embodiment, the states of human organs, which can be determined by electronic devices via sound, are diagnosed, and the diagnosis is provided to a user, so that an early diagnosis may be performed.

Figure 7:
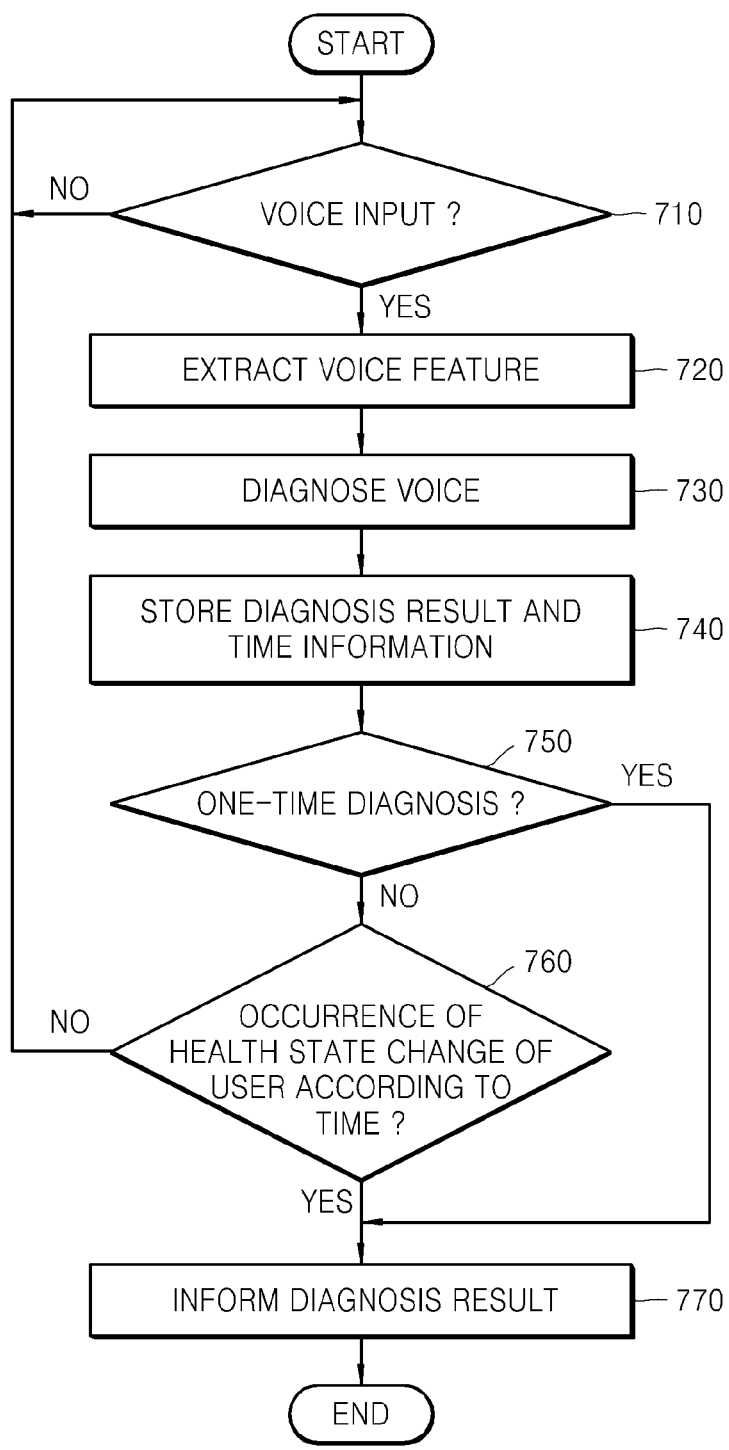
FIG. 7 is a detailed flowchart of a method of diagnosing health, according to another exemplary embodiment.

FIG. 7 is a detailed flowchart of a method of diagnosing health, according to another exemplary embodiment.

It is checked whether a user's voice has been input via a recording or a phone conversation (operation 710).

When it is determined that the user's voice has been input, a voice feature is extracted from the input user's voice (operation 720).

A voice diagnosis is performed by comparing the extracted voice feature with an abnormal state reference (operation 730).

In order to constantly manage a health state, a result of the voice diagnosis and voice diagnosis time information regarding the voice diagnosis are stored (operation 740). The voice diagnosis time information may include a diagnosis date, a diagnosis history, or the like.

A case in which a health state diagnosis is performed in response to a user request may be set as a one-time diagnosis.

It is checked whether a health state diagnosis is a one-time diagnosis (operation 750).

If the health state diagnosis is a one-time diagnosis, a result of the diagnosis is provided to a user, and a treatment appropriate for the result is advised (operation 770).

If the health state diagnosis is not a one-time diagnosis, the health state is constantly monitored by referring to the user's voice. It is constantly checked whether any change in the health state of the user occurs over time (operation 760).

If a change over time occurs in the health state of the user, a result of the diagnosis is provided to the user, and then a treatment appropriate for the result is advised (operation 770).

FIG. 8 is a detailed flowchart of a method of diagnosing health, according to another exemplary embodiment.

It is determined whether a user's voice has been input using a recording or a phone conversation (operation 810).

When it is determined that a user's voice has been input, a voice feature is extracted from the input user voice (operation 820).

A voice diagnosis is performed by comparing the extracted voice feature with an abnormal state reference (operation 830).

In order to constantly manage a health state, a result of the voice diagnosis and voice diagnosis time information regarding the voice diagnosis are stored (operation 840). The voice diagnosis time information may include a voice diagnosis date, a diagnosis history, or the like.

It is determined whether the health state diagnosis is a one-time diagnosis (operation 850).

If the health state diagnosis is a one-time diagnosis, a result of the diagnosis is provided to a user, and a treatment appropriate for the result is advised (operation 852).

Otherwise, if the health state diagnosis is not a one-time diagnosis, the health state is constantly monitored by referring to the user's voice, and any changes over time in the health state of the user is analyzed (operation 860).

Then, different advising messages are displayed according to a change in the user's health state over time.

For example, if the health state change of the user continues for one or two days, a message "Don't overexert yourself" is displayed to the user (operation 862), if the health state change of the user continues for at least three days, it is determined that the user has a short-term disease, and a message advising the user to go to see a doctor is displayed to the user (operation 864), and if the health state change of the user continues for at least two weeks, it is determined that a disease has worsened, and a message strongly advising the user to go to see a doctor is displayed to the user (operation 866).

According to the voice diagnosis, it is determined whether a health state of the user has improved (operation 870).

If the health state of the user has improved, the improvement is provided to the user (operation 880).

Figure 9A:
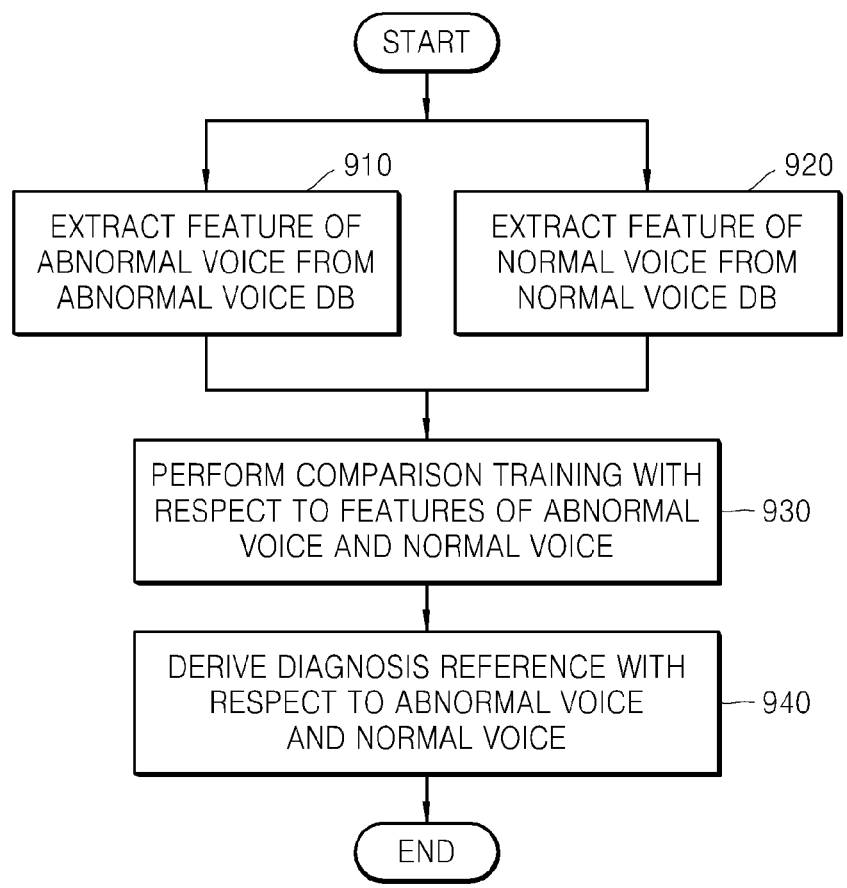
FIG. 9A illustrates a method of deriving references with respect to a normal voice and an abnormal voice of FIG. 6.

FIG. 9A illustrates a method of deriving references with respect to a normal voice and an abnormal voice of FIG. 6.

An abnormal voice database and a normal voice database are formed.

An abnormal voice feature and a normal voice feature are extracted from the abnormal voice database and the normal voice database, respectively (operations 910 and 920).

Comparison training is performed on the abnormal voice feature and the normal voice feature by using an analysis modeling technique (operation 930).

The references with respect to the normal voice and the abnormal voice are derived via the comparison training (operation 940).

FIG. 9B illustrates a diagnosing reference with respect to a normal voice of GMM parameters that are modeled by two Gaussian functions.

Referring to FIG. 9B, the GMM parameters including shimmer, MFCC2, and MFCC3 that are modeled by first and second Gaussian functions to indicate a division with respect to a normal voice and an abnormal voice.

Figure 10:
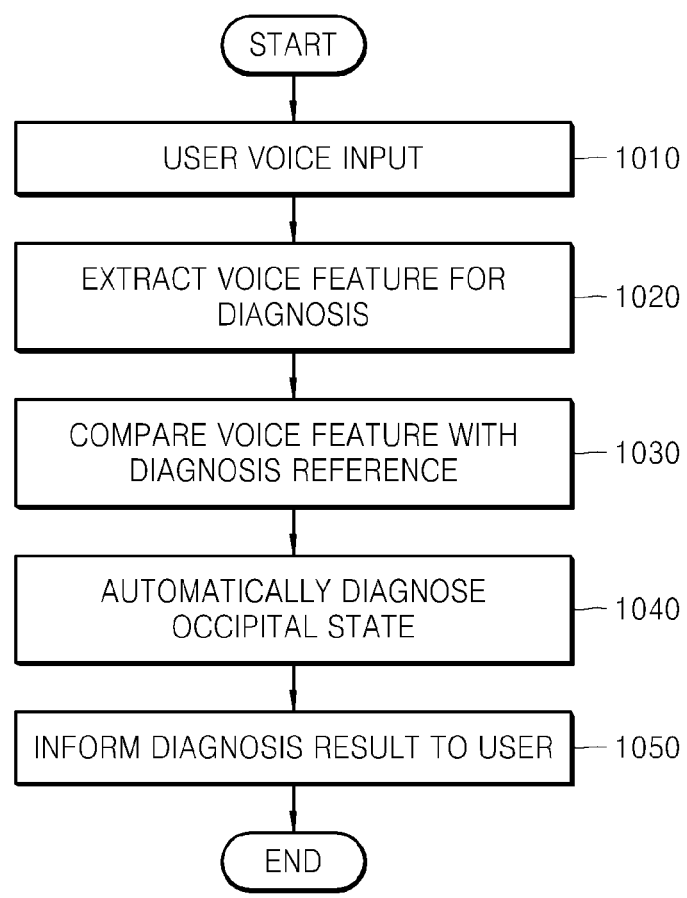

FIG. 10 is a flowchart of a method of diagnosing health, according to another exemplary embodiment.

A user voice is input via a recording or a phone conversation (operation 1010).

A voice feature with respect to an occipital state is extracted from the input user voice (operation 1020).

The extracted voice feature is compared with an abnormal state reference (operation 1030) and then a health state with respect to the abnormal state is automatically diagnosed (operation 1040).

The diagnosis result regarding the health state is provided to a user (operation 1050).

Figure 11:
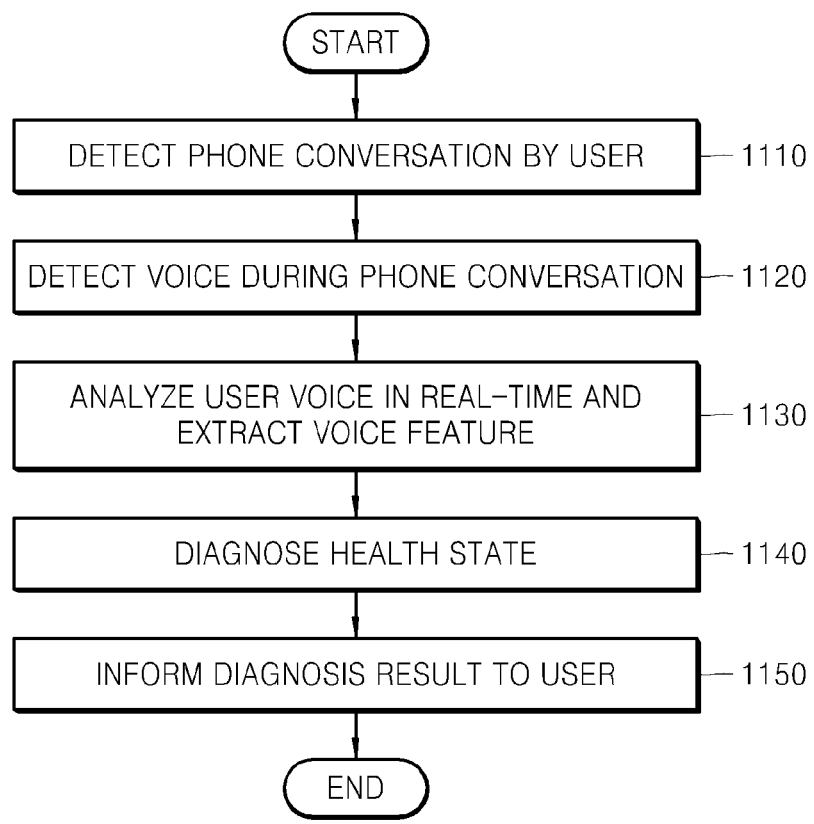
FIG. 11 is a flowchart of a method of diagnosing a state of health by using a mobile phone, according to an exemplary embodiment.

FIG. 11 is a flowchart of a method of diagnosing a health state by using a mobile phone, according to an exemplary embodiment.

A phone conversation of a user is detected by the mobile phone (operation 1110).

A voice of the user during the phone conversation is detected (operation 1120).

The voice of the user during the phone conversation is analyzed in real-time, and a voice feature for diagnosing a health state is extracted from the voice of the user (operation 1130).

The heath state is analyzed using the extracted voice feature (operation 1140).

A result of the diagnosis is provided to the user (operation 1150).

According to the present embodiment, when the user uses the mobile phone, the health state of the user may be automatically diagnosed by using the voice of the user during the phone conversation. Also, whenever the user makes a phone call, the user may store and check the result of the diagnosis.

Exemplary embodiments described herein can be written as computer programs and can be implemented in general-use digital computers that execute the programs using a computer-readable recording medium. Examples of the computer-readable recording medium include magnetic storage media (e.g., ROM, floppy disks, hard disks, etc.), optical recording media (e.g., CD-ROMs, or DVDs), etc.

While exemplary embodiments have been particularly shown and described, it will be understood by those of ordinary skill in the art that various changes in form and details may be made therein without departing from the spirit and scope of the present inventive concept as defined by the following claims.

What is claimed is:

1. A health diagnosing apparatus comprising:
    a voice detecting unit configured to detect a user's voice;
    a voice analyzing unit configured to extract a voice feature from the user's voice detected by the voice detecting unit;
    a voice diagnosing unit configured to diagnose the user's voice by comparing the voice feature extracted by the voice analyzing unit with reference;
    a warning outputting unit configured to output a predetermined warning indication based on a result of diagnosing.

2. The health diagnosing apparatus of claim 1, wherein the voice detecting unit is further configured to monitor changes in a voice state of the user.

3. The health diagnosing apparatus of claim 1, wherein the voice detecting unit comprises:
    an analog-to-digital converter,
    wherein the voice detecting unit is further configured to detect a voice signal from a digital signal output by the analog-to-digital converter.

4. The health diagnosing apparatus of claim 1, wherein the voice analyzing unit comprises:
    a health state selecting unit configured to select a health state type to be diagnosed based on the user's voice detected by the voice detecting unit a voice period selecting unit configured to select a voice period for a diagnosis based on the health state type selected by the health state selecting unit; and a voice feature selecting unit configured to select the voice feature according to the health state type selected by the health state selecting unit; and a voice feature extracting unit configured to extract the voice feature from the user's voice based on the voice feature selected by the voice feature selecting unit.

5. The health diagnosing apparatus of claim 4, wherein the voice feature extracting unit comprises a normal voice database and an abnormal voice database.

6. The health diagnosing apparatus of claim 1, wherein the voice diagnosing unit comprises:

a comparing unit configured to compare the voice feature extracted by the voice analyzing unit with the abnormal state reference;

a monitoring unit configured to detect a change over time in a voice state of the user; and a diagnosis processing unit configured to diagnose a state of the user's health according to a result of the comparison by the comparing unit, and the change detected by the monitoring unit.

7. The health diagnosing apparatus of claim 6, further comprising a storage unit configured to store an output of the diagnosing processing unit and diagnosis time information.

8. The health diagnosing apparatus of claim 1, wherein the diagnosis outputting unit comprises:

a digital signal processor configured to convert information regarding the health state and a health state change diagnosed by the voice diagnosing unit into one or more audio or video signals;

a display unit configured to output a video signal converted by the digital signal processor; and a speaker configured to output an audio signal converted by the digital signal processor.

9. A method of diagnosing a user's health, the method comprising:

detecting and monitoring a voice of the user;

extracting a voice feature from the detected voice;

diagnosing the user's voice by comparing the extracted voice feature with a reference;

outputting a predetermined warning indication based on a result of the comparing.

10. The method of claim 9, wherein the detecting the voice comprises:

converting an input voice into a digital voice signal; and detecting the voice of the user from the digital voice signal.

11. The method of claim 9, wherein the extracting the voice feature comprises:

determining the health state type to be diagnosed;

selecting a voice period for a diagnosis according to the health state type;

selecting a voice feature corresponding to the health state type; and extracting the selected voice feature from the selected voice period.

12. The method of claim 9, wherein the diagnosing the health state further comprises:

analyzing a change over time in the health state; and outputting an advising message according to the change over time in the health state.

13. The method of claim 9, wherein the diagnosing the health state and the monitoring the change in the health state comprise:

comparing the extracted voice feature with the abnormal state reference;

detecting a change over time in a voice state; and diagnosing the health state of the user according to a result of the comparison, and the change over time in the voice state.

14. The method of claim 13, further comprising storing and updating a result of the diagnosing and diagnosis time information in a storage unit.

15. The method of claim 13, further comprising determining references with respect to an abnormal voice and a normal voice.

16. The method of claim 15, wherein the determining the references comprises:

forming an abnormal voice database and a normal voice database;

extracting an abnormal voice feature and a normal voice feature from the abnormal voice database and the normal voice database, respectively:

performing comparison training with respect to the extracted abnormal voice feature and the extracted normal voice feature; and determining the abnormal state reference according to the comparison training.

17. The method of claim 9, wherein the outputting comprises:

converting information regarding the health state and the health state change into one or more audio or video signals; and outputting the one or more audio or video signals.

18. A computer-readable recording medium having recorded thereon a program for executing a method of diagnosing a user's health, the method comprising:

detecting and monitoring a voice of the user;

extracting a voice feature from the detected voice;

diagnosing the user's voice by comparing the extracted voice feature with a reference;

outputting a predetermined warning indication based on a result of the comparing.

* * * * *